(12) United States Patent
Janscha et al.

(10) Patent No.: US 11,028,786 B2
(45) Date of Patent: Jun. 8, 2021

(54) PORTABLE GENERATOR INCLUDING CARBON MONOXIDE DETECTOR

(71) Applicant: Briggs & Stratton, LLC, Wauwatosa, WI (US)

(72) Inventors: Ryan D. Janscha, Brookfield, WI (US); Mark Willer, Brookfield, WI (US)

(73) Assignee: Briggs & Stratton, LLC, Wauwatosa, WI (US)

( * ) Notice: Subject to any disclaimer, the term of this patent is extended or adjusted under 35 U.S.C. 154(b) by 0 days.

(21) Appl. No.: 16/498,816

(22) PCT Filed: Mar. 28, 2018

(86) PCT No.: PCT/US2018/024855
§ 371 (c)(1),
(2) Date: Sep. 27, 2019

(87) PCT Pub. No.: WO2018/183506
PCT Pub. Date: Oct. 4, 2018

(65) Prior Publication Data
US 2020/0040827 A1 Feb. 6, 2020

Related U.S. Application Data

(60) Provisional application No. 62/477,817, filed on Mar. 28, 2017.

(51) Int. Cl.
*F02D 35/00* (2006.01)
*G01N 33/00* (2006.01)
(Continued)

(52) U.S. Cl.
CPC ....... *F02D 35/0015* (2013.01); *G01N 33/004* (2013.01); *G08B 5/36* (2013.01); *G08B 21/14* (2013.01)

(58) Field of Classification Search
CPC .... F02D 35/0015; G01N 33/004; G08B 5/36; G08B 21/14; G08B 21/16; G08B 17/10; G08B 21/18; F02B 63/047
See application file for complete search history.

(56) References Cited

U.S. PATENT DOCUMENTS 3,703,162 A 11/1972 Aono
5,049,861 A 9/1991 Grace et al.
(Continued)

FOREIGN PATENT DOCUMENTS

WO WO-2018/035434 A1 2/2018

OTHER PUBLICATIONS

"Smoke Detector is Beeping Chirping Every 30 Seconds?—How to Reset?," retrieved from https://removeandreplace.com/2015/09/09/smoke-alarm-beeping-chirping-every-30-seconds-how-to-reset/> (May 29, 2009) (Year: 2009).*

(Continued)

*Primary Examiner* — Jacob M Amick
*Assistant Examiner* — Charles J Brauch
(74) *Attorney, Agent, or Firm* — Foley & Lardner LLP

(57) ABSTRACT

A portable generator includes a CO sensor module to sense CO levels in the environment surrounding the portable generator. The CO sensor module senses high levels of CO and sends a signal to shut down the engine on the portable generator. The CO sensor module alerts the user by emitting an LED light whether the CO sensor module is functioning properly, improperly or if high CO levels are detected. The CO sensor module is removable from a control panel of the portable generator to be replaced or maintained by the user per a replacement or maintenance schedule.

12 Claims, 15 Drawing Sheets

(51) Int. Cl.
*G08B 5/36* (2006.01)
*G08B 21/14* (2006.01)

(56) References Cited

U.S. PATENT DOCUMENTS

| | | | |
|---|---|---|---|
| 5,576,739 A * | 11/1996 | Murphy | F27D 19/00 |
| | | | 340/3.4 |
| 5,793,296 A | 8/1998 | Lewkowicz | |
| 6,222,349 B1 | 4/2001 | Lerow et al. | |
| 6,433,696 B1 | 8/2002 | Deiterman et al. | |
| 6,983,726 B1 | 1/2006 | Luo et al. | |
| 8,286,603 B2 | 10/2012 | Sid | |
| 8,375,913 B2 | 2/2013 | Kwiecinski et al. | |
| 8,413,642 B2 | 4/2013 | Johnson et al. | |
| 8,534,258 B2 | 9/2013 | Cristoforo | |
| 8,939,134 B2 | 1/2015 | Sato et al. | |
| 9,058,739 B2 | 6/2015 | Sid | |
| 9,175,601 B2 | 11/2015 | Markoski | |
| 9,293,914 B2 | 3/2016 | Mauk et al. | |
| 2003/0091430 A1 | 5/2003 | Mulera et al. | |
| 2007/0085692 A1 * | 4/2007 | Grant | G08B 21/14 |
| | | | 340/632 |
| 2008/0015794 A1 | 1/2008 | Eiler et al. | |
| 2009/0240377 A1 | 9/2009 | Batzler et al. | |
| 2011/0084844 A1 | 4/2011 | Carnation | |
| 2012/0122040 A1 | 5/2012 | Xu et al. | |
| 2012/0277972 A1 | 11/2012 | Rayl | |
| 2013/0110376 A1 | 5/2013 | Surnilla et al. | |
| 2013/0168969 A1 | 7/2013 | Markoski | |
| 2015/0036138 A1 | 2/2015 | Watson et al. | |
| 2015/0096352 A1 | 4/2015 | Peterson et al. | |
| 2016/0258387 A1 | 9/2016 | Markoski | |
| 2017/0110003 A1 | 4/2017 | Barson | |
| 2017/0363022 A1 | 12/2017 | Tedder et al. | |
| 2018/0291822 A1 | 10/2018 | Wischstadt et al. | |

OTHER PUBLICATIONS

"Smoke Detector is Beeping Chirping Every 30 Seconds?—How to Reset?," retrieved from https://removeandreplace.com/2015/09/09/smoke-alarm-beeping-chirping-every-30-seconds-how-to-reset> (May 29, 2009).

International Search Report and Written Opinion, PCT/US2018/024855, Briggs & Stratton Corporation (Jul. 23, 2018).

* cited by examiner

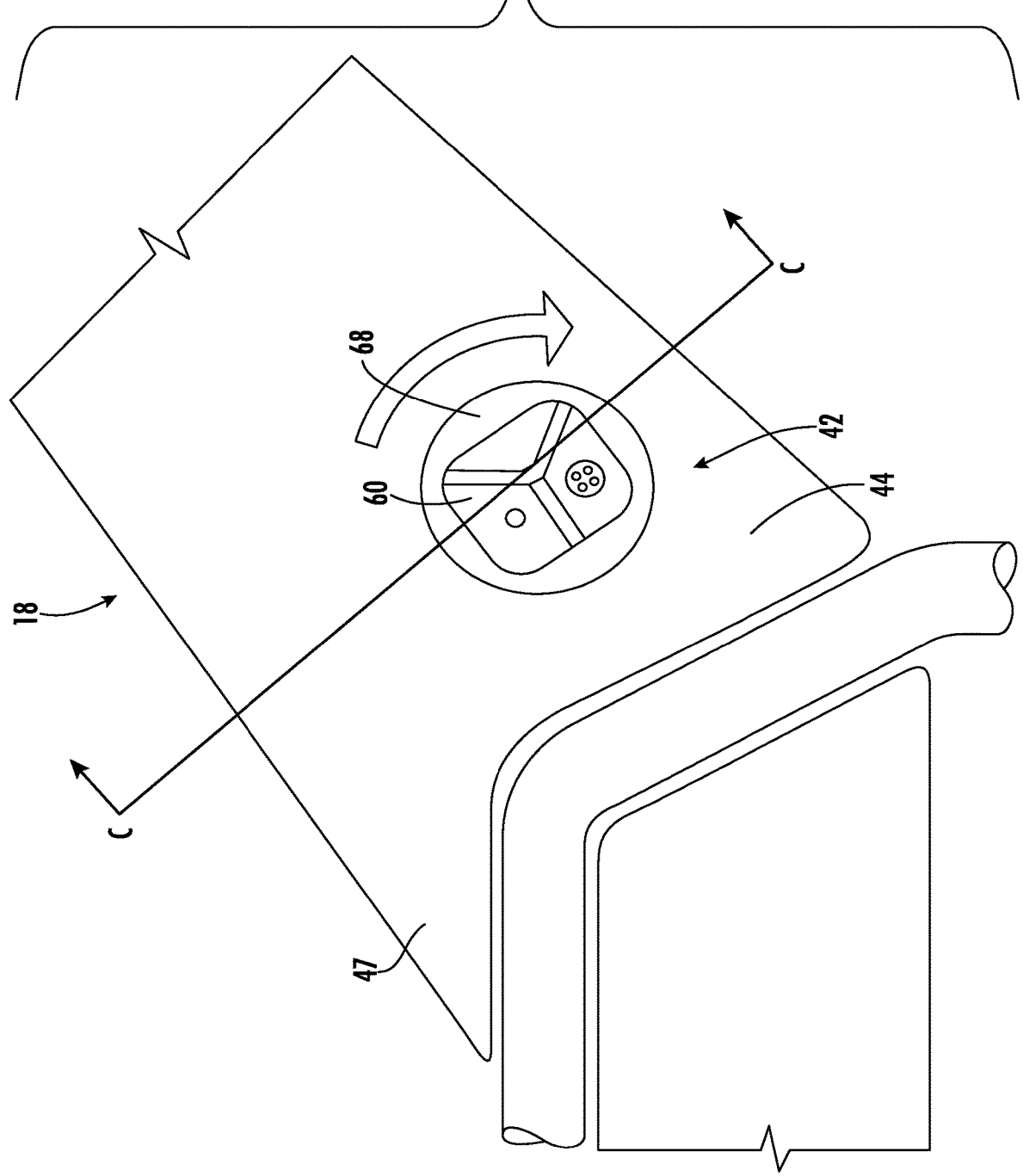

PORTABLE GENERATOR INCLUDING CARBON MONOXIDE DETECTOR

CROSS-REFERENCE TO RELATED PATENT APPLICATIONS

This application is a National Stage Application of PCT/US2018/024855, filed Mar. 28, 2018, which claims the benefit of U.S. Provisional Patent Application No. 62/477,817, filed Mar. 28, 2017, both of which are incorporated herein by reference in their entireties.

BACKGROUND

The present invention generally relates to internal combustion engines and portable generators powered by such engines. Portable generators operating in enclosed or semi-enclosed space produce carbon monoxide gas build-up. Specifically, the present invention relates to carbon monoxide (CO) detection and engine shutdown system for a portable generator.

SUMMARY

One embodiment of the invention relates to a generator. The generator includes an engine, a control panel, and a CO sensor module. The control panel includes a control plate having a control surface and a back side positioned opposite from the control surface and a compartment coupled to the control plate, the compartment and the control plate defining an interior volume. The CO sensor module includes a CO sensor, the CO sensor module positioned to extend through the control plate and into the interior volume of the compartment and removably coupled to the backside of the control plate. The CO sensor module is configured to be removable from the control plate and replaceable with a replacement CO sensor module. The CO sensor is configured to detect CO concentration near the generator.

Another embodiment of the invention relates to a removable and replaceable CO sensor module. The module includes a housing having a first portion and a second portion, the first portion configured to be removably inserted into a compartment of a generator and the second portion configured to be positioned outside of the compartment. The CO sensor module further includes a CO sensor positioned within the first portion of the housing and configured to detect concentrations of CO, a module battery positioned within the housing and configured to power the CO sensor module, wherein the second portion of the housing includes a mounting ring configured to abut a control panel of the generator in an installed position.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures, in which:

FIG. 4B is a perspective view of the control panel of FIG. 4A with the CO sensor module installed;

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring generally to the figures, in one embodiment a carbon monoxide (CO) detection system is incorporated into a portable generator. The CO detection system is in the form of a CO sensor module that may be removable and serviceable by a user. The CO sensor module alerts the user audibly, visually, or both when the CO levels in the surrounding environment reach high levels and shuts off the engine to prevent any additional CO being produced from operation of the engine. For example, the portable generator having a CO sensor module operating within a room that is 1000 cubic feet will be able to detect levels of CO that are considered to be high, e.g., 400 part per million (ppm), and shut the engine down prior to the user being alerted of high levels by an EPA certified CO detector that is located 39" above the floor (assuming the CO detector and the portable generator having the CO sensor module are located in the same area of the room).

Figure 1:
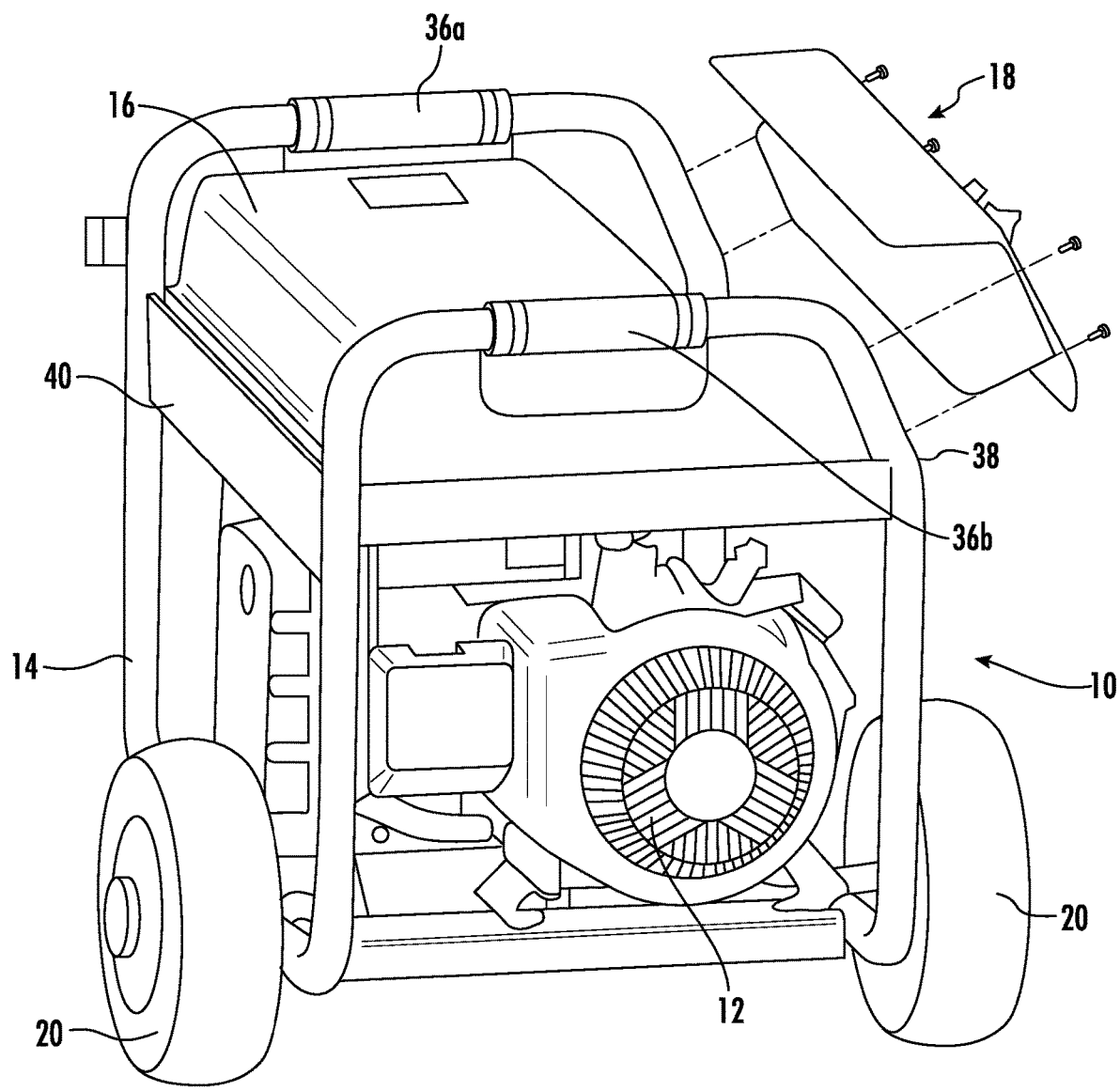
FIG. 1 is an exploded perspective view of a portable generator according to an exemplary embodiment.
Figure 2:
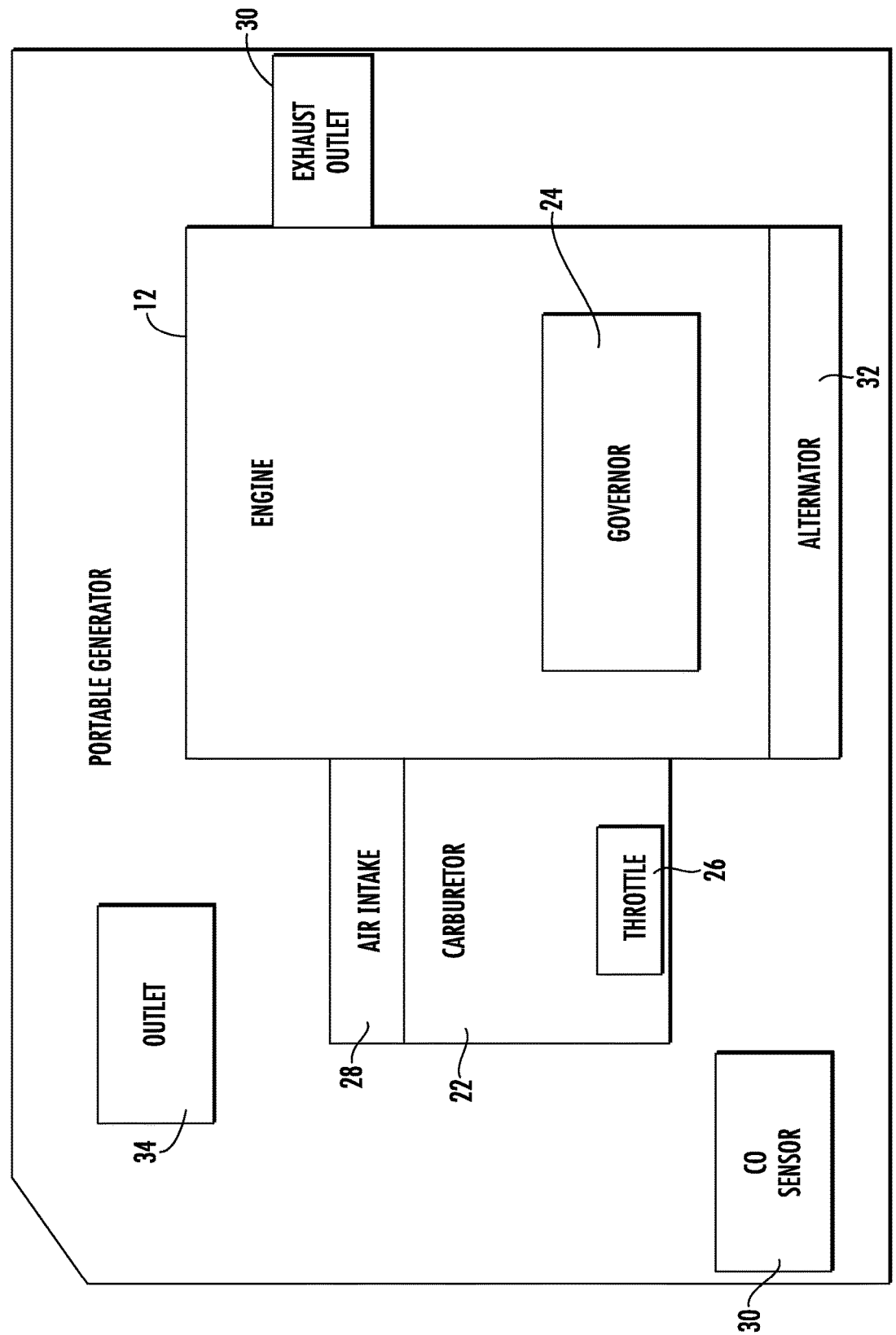
FIG. 2 is a schematic diagram of the portable generator of FIG. 1.

Referring to FIG. 1 and FIG. 2, a generator 10 having a carbon monoxide detection system is shown according to an exemplary embodiment. The generator 10 includes an engine 12, a frame 14, a fuel tank 16, a control panel 18 and a pair of wheels 20. The engine 12 includes a carburetor 22 or other air-fuel mixing device (e.g., electronic fuel injection, direct fuel injection, etc.), a governor 24, a throttle 26, an air intake 28, an exhaust outlet 30 and an alternator 32 driven by the engine 12. The alternator 32 produces electrical power from input mechanical power from the engine 12. The control panel 18 includes an outlet 34 to supply the generated electrical power to an electrical device. The control panel 18 also includes a control plate 47 having a control surface 44 and a back side 48 (e.g., positioned on opposite from the control surface 44), a compartment 46 and a removable CO sensor module 42 (see FIG. 3, FIG. 4A and FIG. 5A) that may be replaceable and serviceable by the user as prescribed by a service/maintenance schedule. The pair of wheels 20 assists the user to manually maneuver the generator 10 from one location to a second location with ease and increase comfort. The frame 14 includes two upper portions 36*a* and 36*b* that extend from a front end 38 of the generator 10 to a rear end 40 of the generator 10. The fuel tank 16 extends a portion of the length between the two upper portions 36*a*, 36*b* above the engine 12 in between the front end 38 and the rear end 40.

Figure 3:
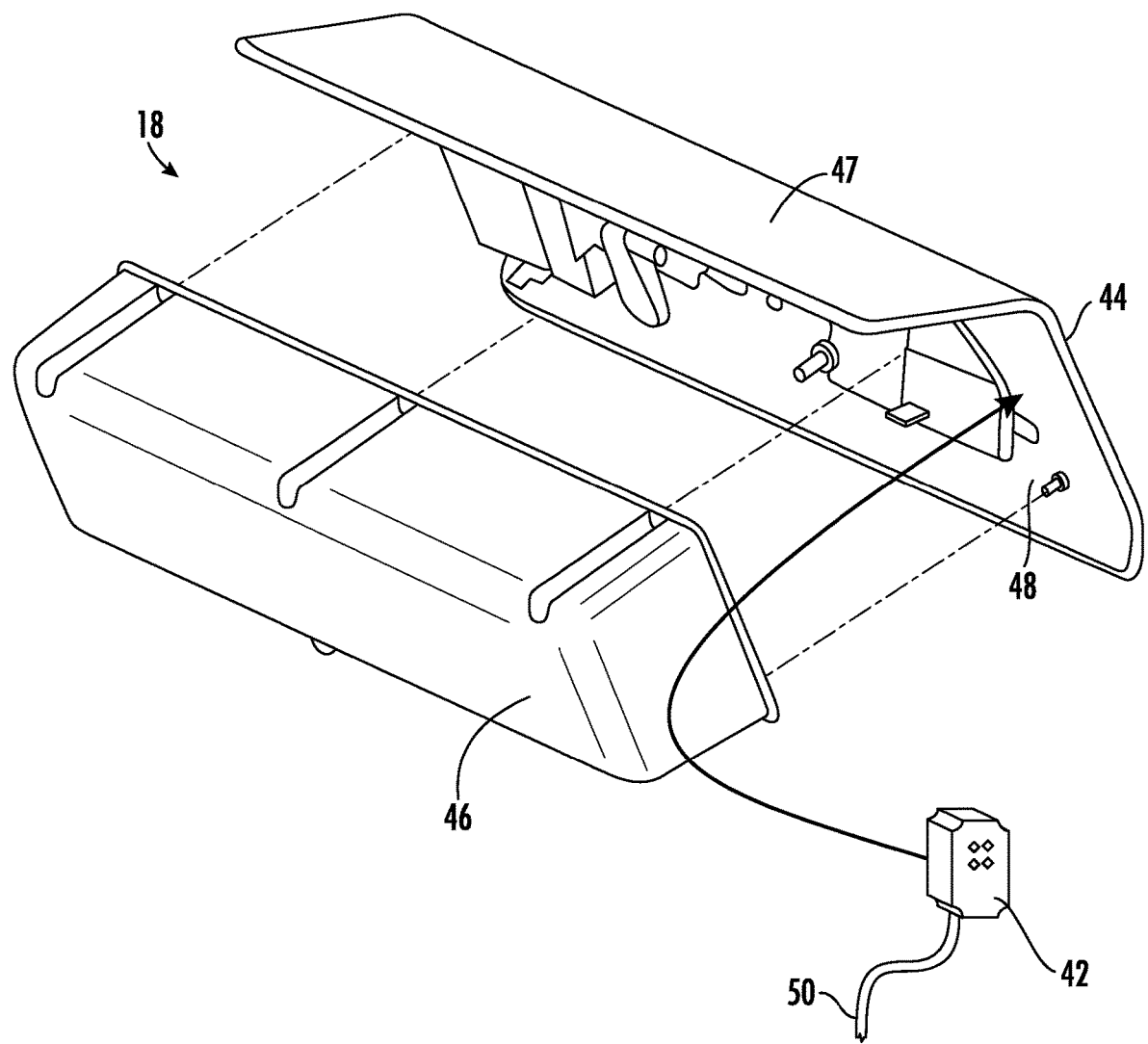
FIG. 3 is an exploded perspective view of a control panel of the portable generator of FIG. 1.

Referring to FIG. 3, the CO sensor module 42 may be removed from the control panel 18 to be serviced and maintained by the user. The user may remove the CO sensor module 42 to replace components such as a CO sensor 80 (see FIG. 4C, FIG. 5G or FIG. 6A) with a new CO sensor 80, replace a module battery 76 (see FIG. 4C or FIG. 5G) with a new module battery 76, or perform any other routine maintenance that may be required by the CO sensor module 42. The user may then insert the CO sensor module 42 back into the control panel 18 and lock or fasten the CO sensor module 42 into a locked and stationary position and resume operation of the portable generator 10.

Referring to FIG. 3, the CO sensor module 42 is shown incorporated into a back side 48 of the control panel 18. The control plate 47 and the compartment 46 are fastened together with a plurality of bolts, screws, or any other type of fastening device that may couple the control plate 47 to the compartment 46. The control plate 47 and compartment 46 define an interior volume therein. The connection between the control plate 47 and the compartment 46 is waterproof to prevent moisture from accessing the interior between the control plate 47 and the compartment 46. The CO sensor module 42 extends through the control plate 47 and into the interior volume of the compartment 46 and is removably coupled to the back side 48 of the control plate 47. In some embodiments, a bracket (not shown) mounts the CO sensor module 42 to the back side 48 of the control panel 18 and is located between the back side 48 and the compartment 46. The CO sensor module 42 also includes a circuit 50 that connects to an ignition interrupt circuit (not shown) that shuts down the engine 12 if the CO sensor module 42 senses high levels of CO.

Figure 4A:
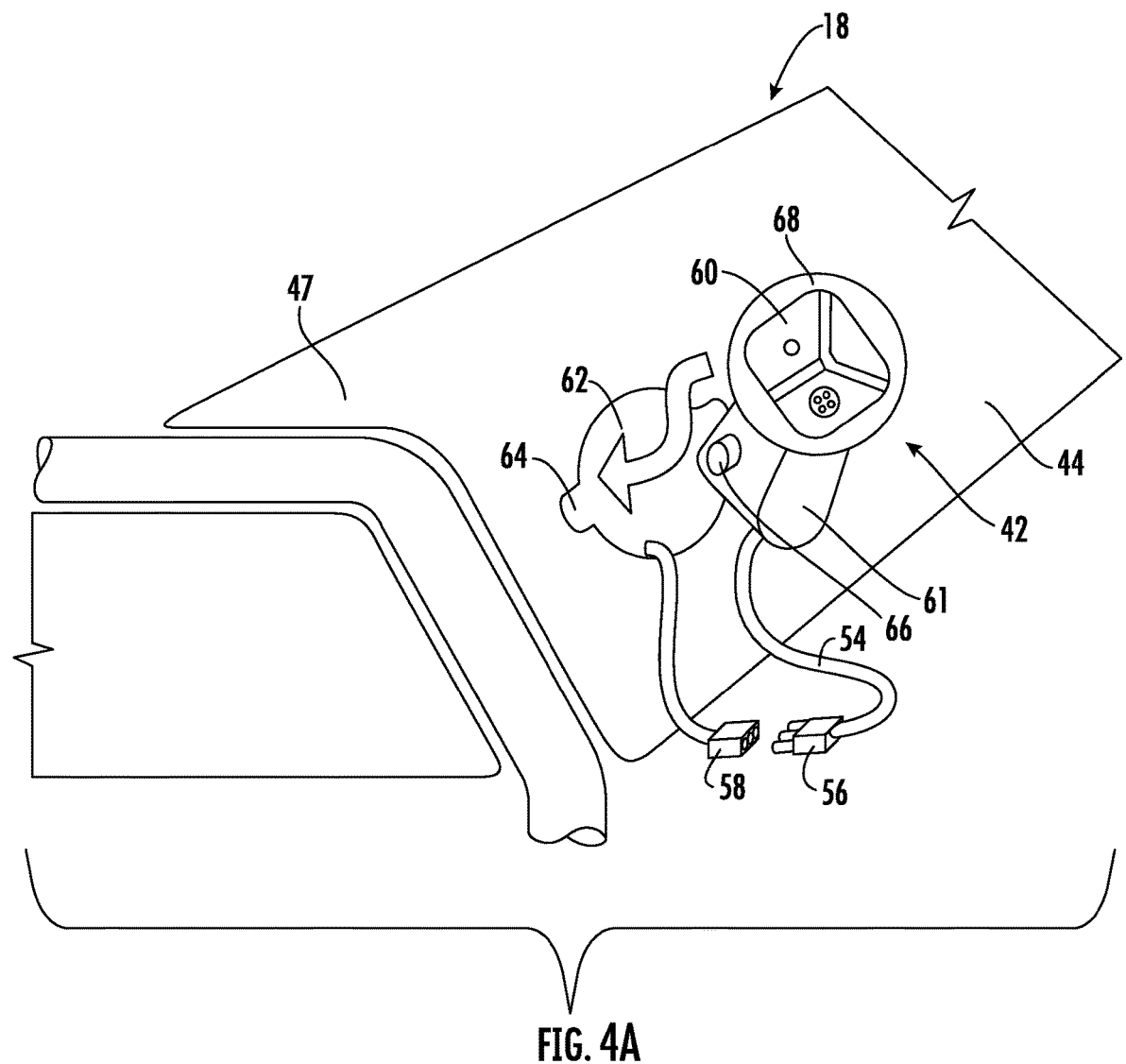
FIG. 4A is an exploded perspective view of the control panel of the portable generator and a CO sensor module according to another exemplary embodiment.
Figure 5A:
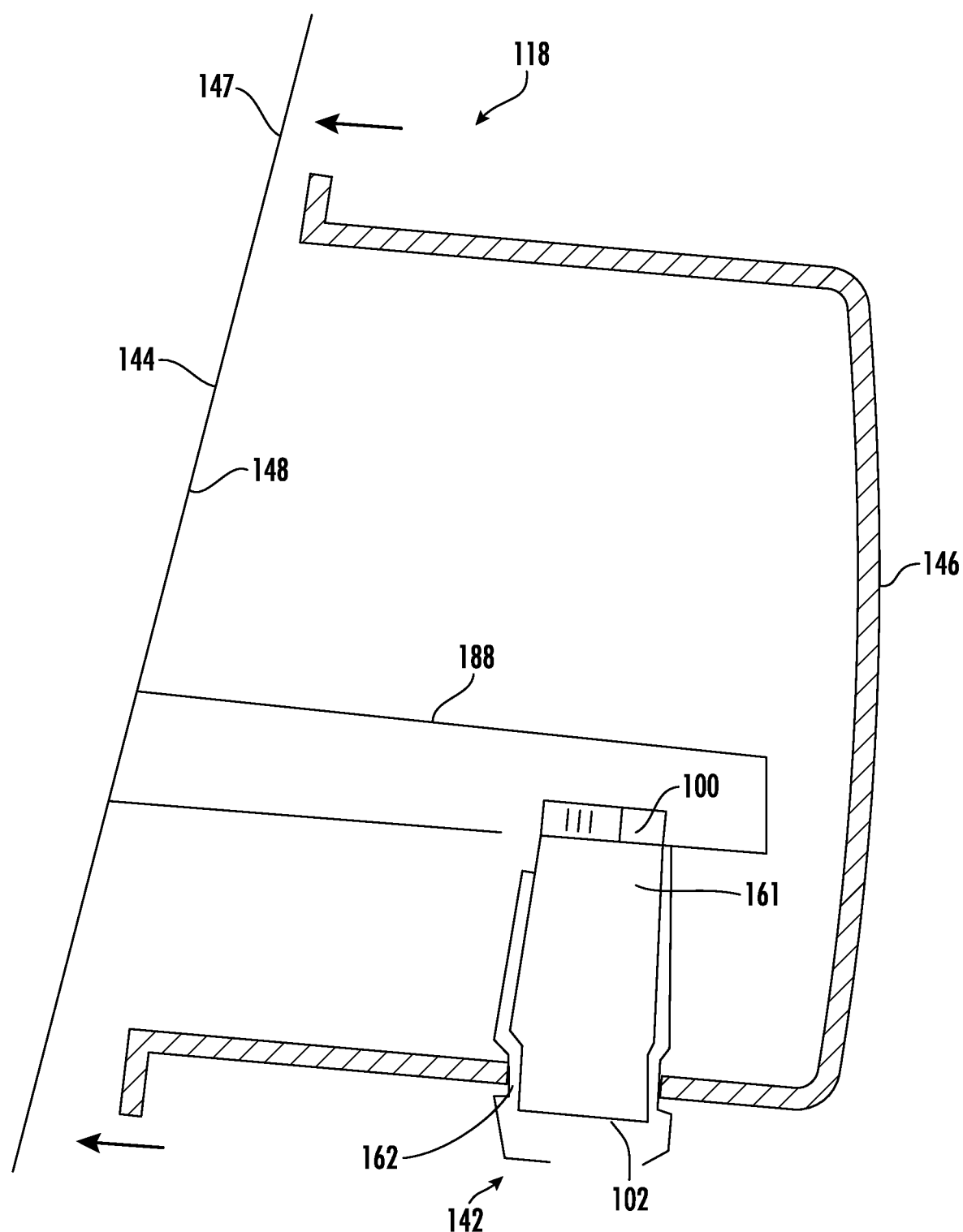
FIG. 5A is a cross-section view of the control panel having a CO sensor module installed within the control panel according to another exemplary embodiment.

Referring to FIG. 4A, the CO sensor module 42 installed through the control surface 44 of the control plate 47 is easily removed from the control panel 18 and replaced with another CO sensor module 42 by the individual user. The CO sensor module 42 includes a cord 54, e.g., a power whip cable, having a module wire harness 56 configured to be inserted into an engine wire harness 58 connected to the engine 12. The connection between the module wire harness 56 and the engine wire harness 58 permits the user to be able to start the engine 12. The disconnection between the module wire harness 56 and the engine wire harness 58 or removing the CO sensor module 42 from the control panel 18 places the ignition of the engine 12 in an inoperative condition, grounding the primary ignition, not allowing the engine 12 to start. Requiring the connection to be made between the module wire harness 56 and the engine wire harness 58 prevents the user from intentionally removing the CO sensor module 42 from the control panel 18. In alternative embodiments, the engine wire harness 58 may include metallic contacts sprung and held in a closed or conducting state when the engine wire harness 58 is not connected with the module wire harness 56. The connection between the module wire harness 56 and the engine wire harness 58 causes a non-conducting separator in the module wire harness 56 to separate the contacts in the engine wire harness 58 to create an open ignition-to-ground circuit and permitting the generator to be in an operative state. In alternative embodiments, a limit switch (not shown) mounted to the control panel 18 may be used that is mechanically activated by the presence of the CO sensor module 42 properly inserted in the control panel 18. In alternative embodiments, other mechanical devices, senses or switches may be provided to detect the CO sensor module is in proximity with the device, switch or sensor. For example, a Hall Effect sensor may be used to detect the presence of the CO sensor module 42.

Referring to FIG. 4A and FIG. 4B, the CO sensor module 42 is shown disconnected from the control panel 18 and installed in the control panel 18, respectively. The CO sensor module 42 includes a housing 61 that inserts into an opening 62 located on the control surface 44 of the control plate 47. The opening 62 includes a recessed portion 64 that is configured to receive a projection 66 extending from the housing 61 of the CO sensor module 42. The housing 61 includes a first portion configured to be inserted into the interior volume of the compartment 46 and a second portion configured to be positioned outside the interior volume. The first portion can include the projection 66. The CO sensor module 42 may be lowered into the control panel 18 through the opening 62 once the projection 66 is properly aligned with the recessed portion 64 until a mounting ring 68 (e.g., included in the second portion) abuts with the control surface 44 of the control plate 47. The CO sensor module 42 may then be turned or twisted 90 degrees in the clockwise direction to lock the CO sensor module 42 into a stationary position (e.g., locked position). As such, the CO sensor module 42 is rotatable between a locked and an unlocked position. In alternative embodiments, the CO sensor module 42 may be turned less than 90 degrees or more than 90 degrees to lock into place or may be twisted in the counter-clockwise direction. In additional alternative embodiments, the CO sensor module 42 may be fastened to the control panel 18 with a plurality of screws, bolts, snap fits, adhesives or another type of fastening device or adhering material that is able to keep the CO sensor module 42 secured in a stationary position after the CO sensor module 42 is inserted into the opening 62.

Figure 4C:
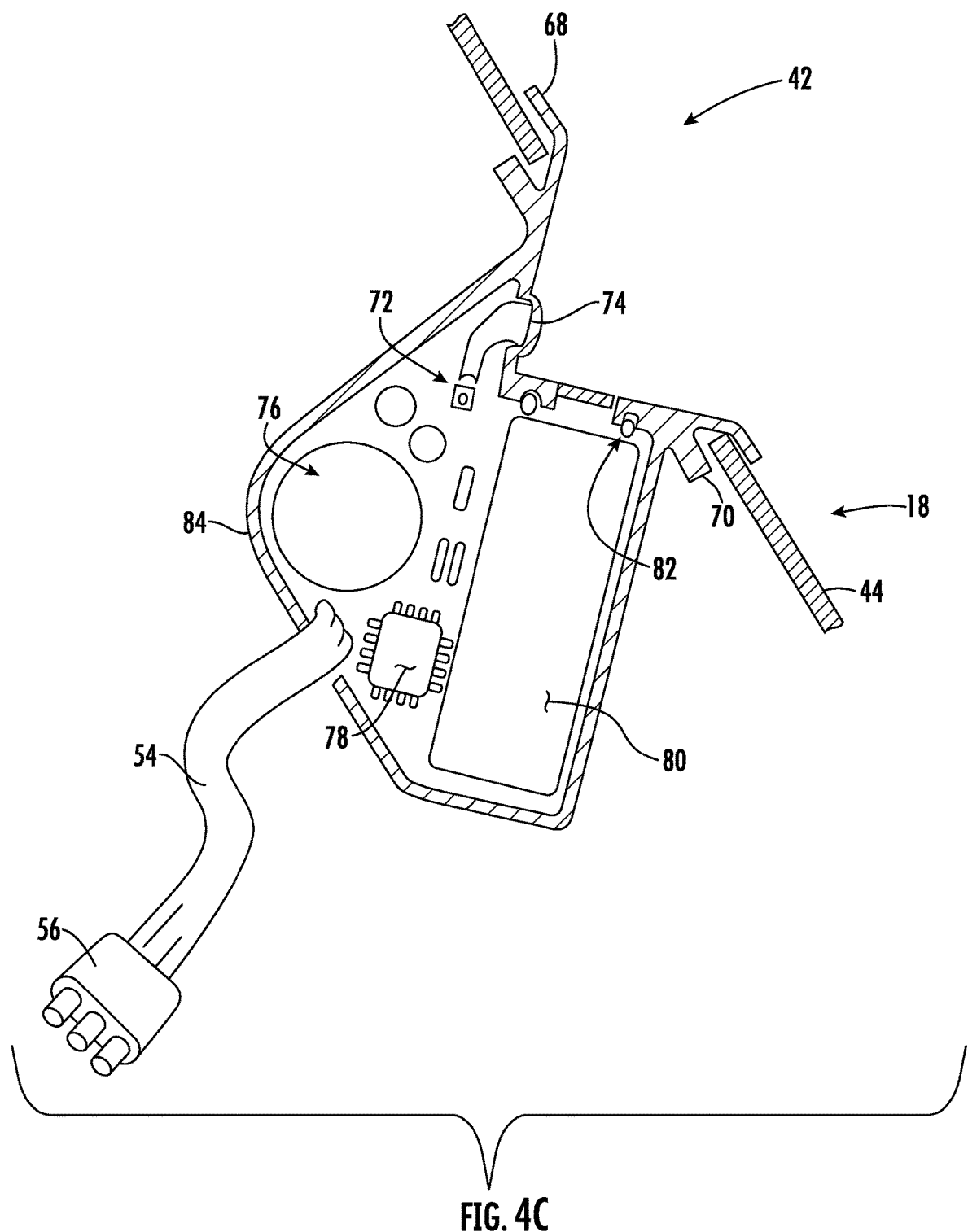
FIG. 4C is a cross-section view of the CO sensor module installed in the control panel along section line C-C in FIG. 4B.

Referring to FIG. 4C, the CO sensor module 42 further includes a retention ring 70, a LED light 72, a light pipe 74, the module battery 76, a microprocessor unit 78, a printed circuit board (PCB) 86 (not shown), a CO sensor 80, an O-ring 82 and a module frame 84. The retention ring 70 assists with maintaining the CO sensor module 42 in a secure position within the control panel 18 and preventing the CO sensor module 42 from becoming loose and possibly falling out of the control panel 18 during operational and non-operational periods erroneously. The O-ring 82 forms a waterproof seal between the CO sensor 80 and the exterior of the CO sensor module 42 protecting the CO sensor 80 from water intrusion and preventing damage to the CO sensor 80. The PCB 86 includes a protective chemical coating or polymer, e.g., a conformal coating, to protect the electronic circuits from the surrounding environment. The LED light 72 is a visual indicator to alert the user that the life of the battery 76 is degrading, the CO sensor 80 is sensing CO, the life of the CO sensor is degrading, the microprocessor unit 78 is defective, or another aspect of the CO sensor module 42 may be malfunctioning. The LED light 72 may indicate to the user all of these conditions, a combination of the conditions, or only a single condition is present in the CO sensor module. For example, the LED light 72 may indicate to the user that the module battery 76 or the CO sensor 80 may be expiring in a certain time period, e.g., 6-months, or the LED light 72 may only be an indicator that the CO sensor 80 is sensing CO levels in the surrounding environment. The light pipe 74 projects light emitted from the LED light 72 to be visible to the user. The LED light 72 emitted through the light pipe 74 may alert the user by a pattern of blinks, the color of the LED light 72 may change from one color to another color, or a combination of both changing colors and blinking patterns to serve as an indicator to the user.

Referring to FIG. 4C, the CO sensor module 42 may be powered by the module battery 76. In the exemplary embodiment a plurality of batteries 76 are connected in parallel to optimize performance and life expectancy of the batteries 76. The CO sensor module 42 may be supplied to a user with the batteries 76 pre-installed.

By having the battery 76 incorporated into the CO sensor module 42, the CO sensor module 42 is capable of sensing CO levels in the environment of the portable generator 10 during non-operational periods of times. This is beneficial to the user that may be attempting to start the portable generator 10 in a high CO level environment. The user may attempt to start the engine 12 on the portable generator 10, but due to the CO sensor module 42 sensing high levels of CO, the CO sensor module 42 prevents the engine 12 from being able to start. The LED light 72 will also be emitting light, providing the user with a visual cue that the environment and nearby surrounding area is experiencing high levels of CO. During operational periods of the portable generator 10, the portable generator 10 may power the module battery 76 of the CO sensor module 42. The life of the module battery 76 is extended by being able to power the CO sensor module 42 with both the module battery 76 and the portable generator 10 by requiring less power from the module battery 76 during operational periods of the portable generator 10. The module battery 76 may be easily removed from the CO sensor module 42 and replaced with another module battery 76. In this way, the CO sensor module 42 can be used on various non-power generating equipment, such as lawn mowers, power washers, etc. In alternative embodiments the module batteries 76 in the CO sensor module 42 do not need to be replaceable. In alternative embodiments various other types of batteries/coin cells may be used to power the CO sensor module 42. In alternative embodiments the module batteries 76 may be supplied separately from the CO sensor module 42 requiring the user to obtain the module batteries 76 and install or replace the module batteries 76 into the CO sensor module 42. In an alternative embodiment, the module batteries 76 and the CO sensor module 42 may not be independently replaceable. For example, the module batteries 76, the CO sensor 80 and the CO sensor module 42 all need to be replaced at the same time as opposed to being replaced in intervals.

Referring to FIG. 4C, the CO sensor 80 located in the CO control module 42 is shown in a substantially vertical position and located below the control surface 44 of the control plate 47. In the exemplary embodiment, the CO sensor 80 is an electrochemical CO sensor having a liquid electrolyte. By having the CO sensor 80 in the substantially vertical orientation allows the liquid electrolyte to expand during freezing conditions. The CO sensor 80 requires anti-polarization and a JFET or resistor to ensure working electrode is connected to common electrode when the CO sensor is in a sleep mode (sleep mode discussed in more detail below). In alternative embodiments, the CO sensor 80 may be oriented in a more horizontal orientation or in a perpendicular direction relative to the control plate 47. In alternative embodiments the CO sensor module may have metal oxide CO sensors or other technology.

In some embodiments, the generator 10 includes a redirect channel or conduit assembled as part of the generator 10 to route exhaust gases exiting the exhaust outlet 30 to the CO sensor 80. The redirect channel directs the exhaust gases (or a portion of the exhaust gases) to the CO sensor 80 upon exiting the exhaust outlet 30 (or prior to exiting the exhaust outlet 30). As such, the redirect channel allows for testing of the CO sensor 80 installation and operation prior to shipment of the generator 10 and/or CO sensor 80 to an end customer by sending exhaust gases to the sensor 80 to verify proper response from the sensor 80 in the presence of exhaust gases. After testing and ensuring the CO sensor 80 works properly, the redirect channel may be plugged or removed to ensure that no false shutdowns or indications occur due to the redirect channel when the generator 10 is in normal use. In other embodiments, the generator 10 does not include a redirect channel.

Referring to FIG. 4C, the microprocessor unit 78 may operate on an ultra-low power, e.g., 350 nA during a standby mode/sleep mode or non-operational periods or 100 µA during an active mode or operational periods. The voltage required by the microprocessor unit 78 is suitable for a 20 mm coin cell battery between 1.8V and 3.6V. The microprocessor unit 78 also includes an on-board analog to digital converter (not shown) and an on-board transimpedance op-amp for amperage to voltage conversion (not shown).

The CO sensor module 42 also includes additional batteries, a detection circuit battery (not shown) and an alert circuit battery (not shown). The detection circuit battery supplies power to the CO sensor 80, the microprocessor 78 and a shutdown latching PCB relay (not shown). The alert circuit battery supplies power to the LED indicator. In alternative embodiments the detection circuit battery and alert circuit battery may supply power to additional features or the detection circuit battery may supply power to less features. In some embodiments, the module battery 76, alert circuit battery, and/or the detection circuit battery may include high-capacity capacitors (e.g., supercapacitor) to prevent power loss when the generator 10 is off.

The CO sensor module 42 includes multiple operational modes, including a pre-activation mode, an active mode and a sleep mode. The CO sensor module 42 is in the pre-activation mode during shipment from a supplier to preserve the module battery 76 power. During the pre-activation mode, the CO sensor 80 does not detect CO. The module batteries 76 are installed in the CO sensor module 42 during shipment and the microprocessor unit 78, the CO sensor 80 and additional components are in the sleep mode. The engine 12 of the portable generator 10 will not start if the CO sensor module 42 is in the pre-activation mode. A DIP switch (not shown) is used to change operational modes. For example, the DIP switch may be used to change the CO sensor module 42 from the pre-activation mode to the active mode or to the sleep mode by pulling a tab to activate the DIP switch.

The CO sensor module 42 detects the presence or lack of AC output voltage from the generator. The CO sensor module 42 is in the active mode when AC output voltage is detected or the portable generator 10 has not detected an AC output voltage for less than 15 minutes. The CO sensor module 42 begins taking CO level readings within 10 seconds of starting the engine 12 on the portable generator 10, switching the mode on the portable generator 10 from the sleep mode to the active mode. During the active mode, the CO sensor module is taking a CO level reading every 0.1 seconds (10 Hz) at a minimum. If there is high levels of CO detected, more than 300 ppm, during the active mode, then the CO sensor module 42 sends a signal to ground the portable generator 10 ignition and to activate the LED light 72 by emitting a steady red light through the light pipe 74. In alternative embodiments, the CO sensor module 42 may take CO level readings more than or less than every 0.1 seconds. In alternative embodiments, the LED light may emit a different color during the active mode to alert the user the CO sensor module 42 detects high CO levels, e.g., blue, yellow, orange, purple, etc. In alternative embodiments, the LED light 72 may not emit a steady light during high CO level detected periods, e.g., the LED light 72 may blink.

The CO sensor module 42 is in the sleep mode when an AC output voltage is not detected for a period of time that is greater than 15 minutes. During the sleep mode, the CO sensor module 42 is taking a CO level reading every 3 minutes. If there is high levels of CO detected, more than 300 ppm, during the sleep mode, then the CO sensor module 42 sends a signal to ground the portable generator 10 ignition and to activate the LED light 72 by emitting a rapidly blinking red light through the light pipe 74. In alternative embodiments, the CO sensor module 42 may be in sleep mode in less than or greater than 15 minutes from detecting an AC output voltage. In alternative embodiments, the CO sensor module 42 may take CO level readings more than or less than every 3 minutes. In alternative embodiments, the LED light 78 may emit a different color during the sleep mode, e.g., blue, yellow, orange, purple, etc., to alert the user the CO sensor module 42 detects high CO levels. In alternative embodiments, the LED light 78 may blink slowly or be on without blinking to alert the user of high CO levels.

The CO sensor module 42 is equipped to perform self-diagnostic testing to determine low detection circuit battery, low alert circuit battery, CO sensor 80 is missing, CO sensor 80 circuitry shorted, or the electrolyte in the CO sensor 80 dried out. During the sleep mode, the CO sensor module will perform self-diagnostic testing every 30 minutes at a minimum. During the active mode, the CO sensor module will perform self-diagnostic testing every 10 minutes at a minimum. Self-diagnostics will not be performed when the CO sensor module 42 initially switches to the active mode to prevent a degraded startup response in the portable generator 10. In alternative embodiments, the CO sensor module 42 may perform the tests during different intervals during both the active mode and the sleep mode.

The CO sensor module 42 alerts the user that the CO sensor module 42 is functioning properly by the LED light 72 emitting a blinking yellow light every 15 seconds. The CO sensor module 42 sends a signal to ground the portable generator 10 ignition and the LED light 72 emits a constant blinking yellow light through the light pipe 74 when a malfunction is detected. In alternative embodiments, the LED light 72 emitted through the light pipe 74 may be a different color, e.g., red, orange, blue, purple, green, etc. when either the CO sensor module 42 is functioning properly or improperly. In alternative embodiments, the LED light 72 may blink more than or less than every 15 seconds or not blink at all.

The CO sensor module 42 also includes a hydrophobic barrier (not shown) to prevent condensing atmospheres from blocking the CO sensor 80. A permeable membrane (not shown), e.g., a decal, is applied on the control panel 18 over the opening 62 to prevent dust and debris from blocking the CO sensor 80. The CO sensor module 80 includes a thermistor compensation circuit (not shown) to contain temperature compensation of ppm values. In alternative embodiments, a gain scaled software table programmed on the microprocessor 78 may be used.

The CO sensor module 42 includes a shutdown circuit (not shown) that calculates and monitors the variance in the sensed CO levels of the environment surrounding the portable generator 10. The shutdown circuit is able to determine whether the portable generator 10 is in an enclosed space experiencing rising levels of CO levels or in an open space and experiencing exhaust backwash over the CO sensor 80 due to a change in wind direction. By being able to calculate and determine whether the CO sensor module 42 is in an open space or an enclosed space minimizes the possibility of nuisance shutdowns.

In some embodiments, the shutdown circuit is communicably and operatively coupled to a wiring harness coupled to an electronic control unit (ECU). The ECU is configured to control the operations of the generator 10. Thus, the ECU is capable of completing a shutdown procedure for the generator 10. The wiring harness is configured to interface with the ECU and communicate potential shutdown signals received from the shutdown circuit. In this situation, a bipolar junction transistor (BJT) opto-isolator is used to relay the communication to the ECU. In other embodiments, the shutdown circuit 54 is communicably and operatively coupled to a wiring harness coupled to the ignition of the generator 10. The shutdown procedure can include grounding the ignition for a period of time (e.g., 10 seconds) until the engine 12 is turned off. In this situation, an opto-isolated triode for alternating current (TRIAC) is used to ground the ignition for a period of time to accomplish a shutdown. Depending on whether the engine has an ECU or not, the appropriate output from the shutdown circuit can be used. In some embodiments, both outputs are included in the CO sensor so that the same sensor may be used with different types of engines, either as original equipment or as an after-market addition to the generator 10.

In some embodiments, an output circuit is provided to gather the operations and provide the operations to a communication output such that a user may connect a device to the output to determine the operations and outputs of the CO sensor. The communication output includes a serial communication interface allowing for connection to the CO sensor for reception and transmission of data. As an example, a device connected to the communication output can receive and decode a generated light blink pattern to determine a fault code associated with the light pattern.

The CO sensor module 42 may also be a retrofittable kit in the form of a brick or disc that may be affixed to portable generators not having the opening 62 in the control panel 18 to receive the housing 61 of the CO sensor module 42. The CO sensor module 42 may also utilize the outlet 34 by having a receiving end for a cord to detect whether the portable generator 10 is in the active mode and begin gathering CO level readings.

Figure 5B:
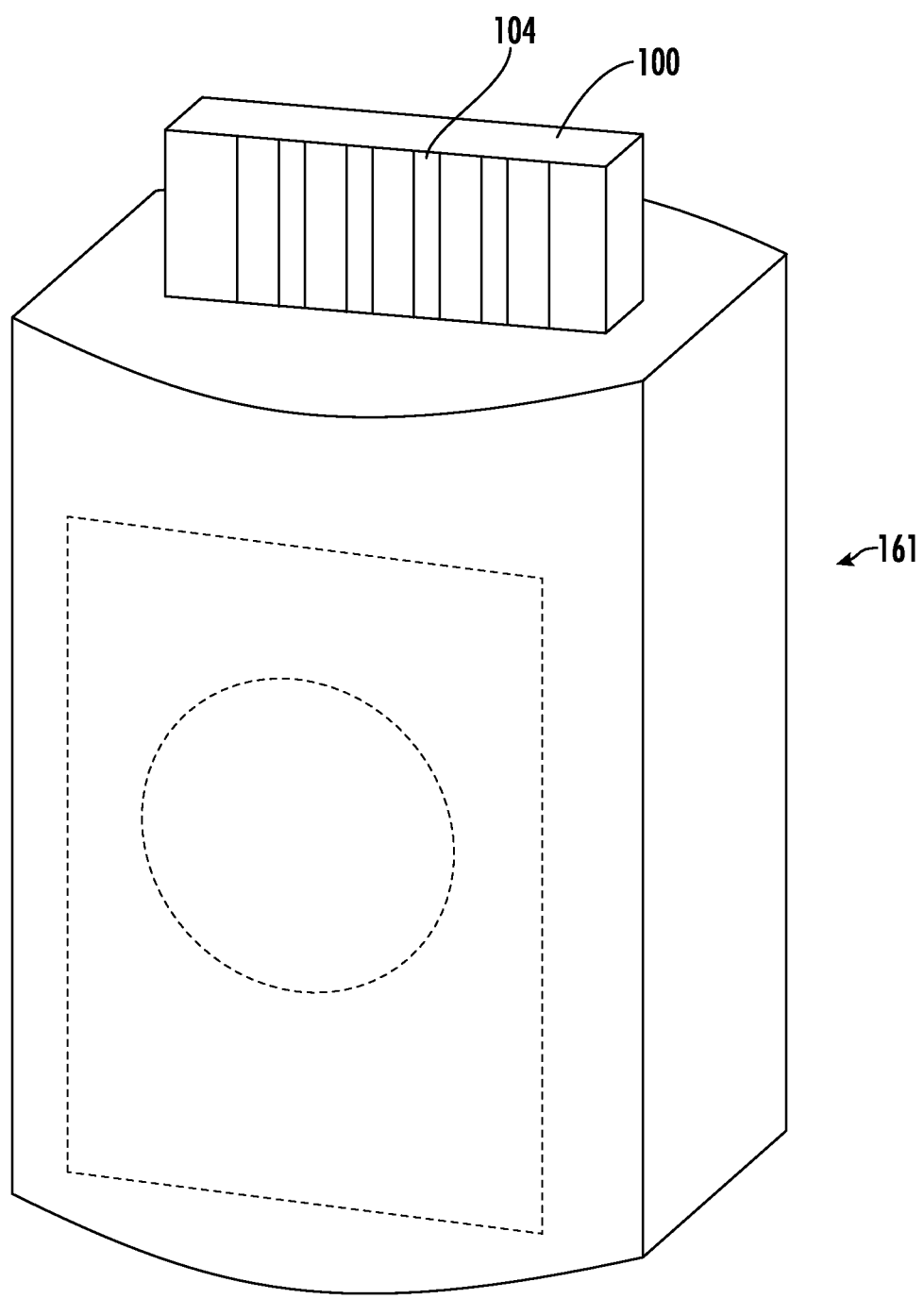
FIG. 5B is a perspective view of a housing included in the CO sensor module in FIG. 5A.
Figure 5C:
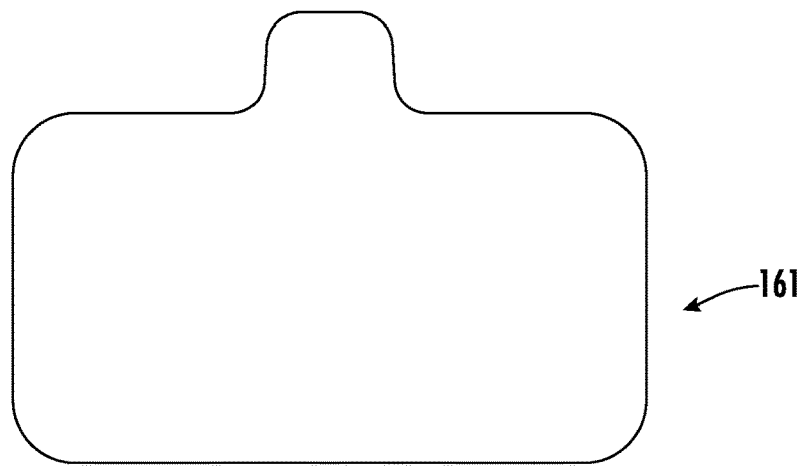
FIGS. 5C-5E are cross-sections of the housings included in the CO sensor module in FIG. 5A.
Figure 5D:
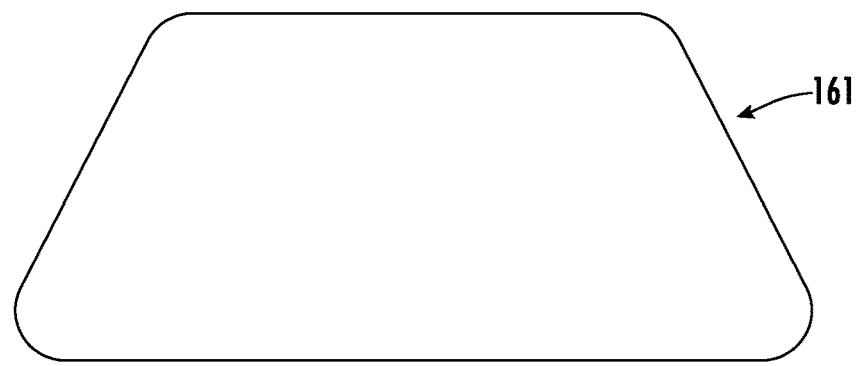
Figure 5E:
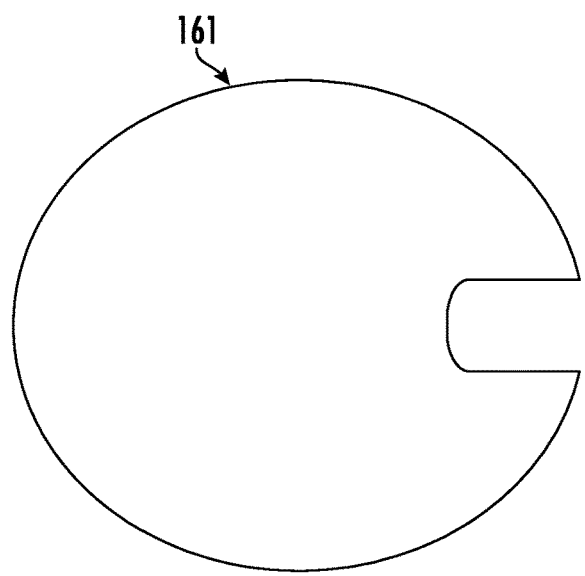

Referring to FIGS. 5A-5I, another exemplary embodiment is shown of the CO sensor module 142 associated with the control plate 147. The CO sensor module 142 shown in FIG. 5A includes a main board 188 extending from the back side 148 of the control plate 147. A portion of the main board 188 is configured to receive a portion of the housing 161 within the interior of the compartment 146. The housing 161 includes an upper end 100 and a lower end 102. The lower end 102 of the housing extends beyond the compartment 146. The upper end 100 of the housing 161 is configured to pass through an opening 162 (see FIG. 5H) and be configured to be inserted into a receiving port (not shown) in the main board 188 to establish an electrical connection. A more detailed view of the housing 161 is shown in FIG. 5B. The upper end 100 of the housing 161 includes a plurality of traces 104 configured to be inserted into the receiving port. The housing 161 is rectangular in shape in the exemplary embodiment. In alternative embodiments shown in FIGS. 5C-5E, the housing 161 may be different configurations, e.g., polygonal, circular, trapezoidal, spherical, oval, etc. and may also include one or more recesses or projections. The housing 161 and the opening 162 may also include projections or recesses to prevent the housing 161 from being installed into the main board 188 improperly. For example, the opening 162 may have a projection and the housing 161 may have a corresponding recess permitting the upper end 100 of the housing 161 to pass through into the interior of the compartment 146.

Figure 5F:
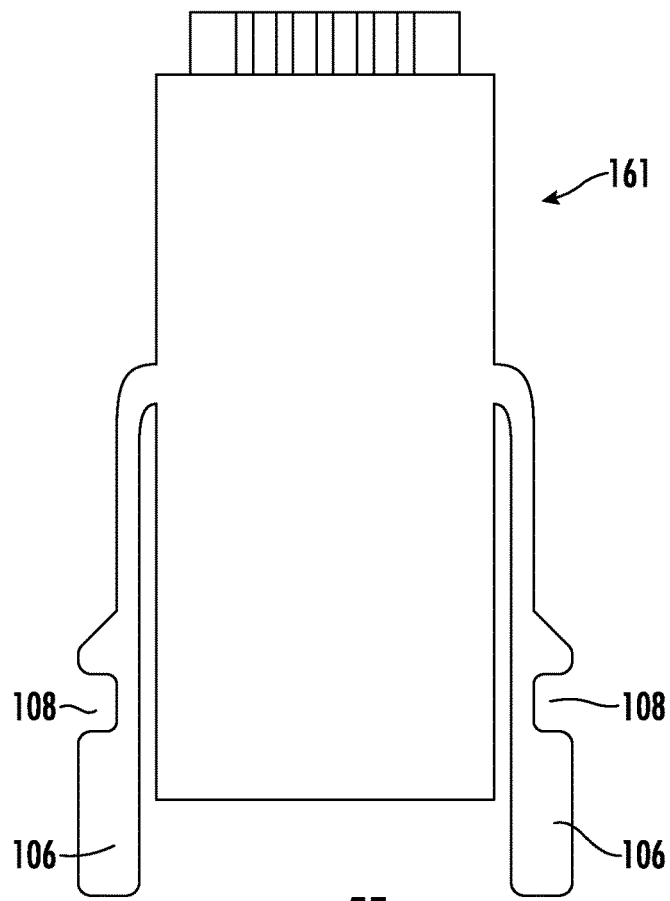
FIG. 5F is a front view of the housing included in the CO sensor module in FIG. 5A.
Figure 5G:
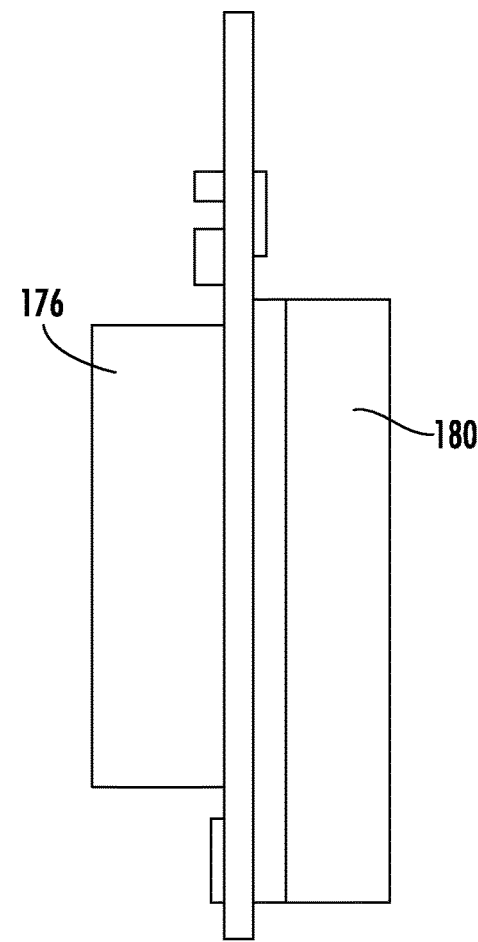
FIG. 5G is a side view of the CO sensor module in FIG. 5A with the housing removed.
Figure 5H:
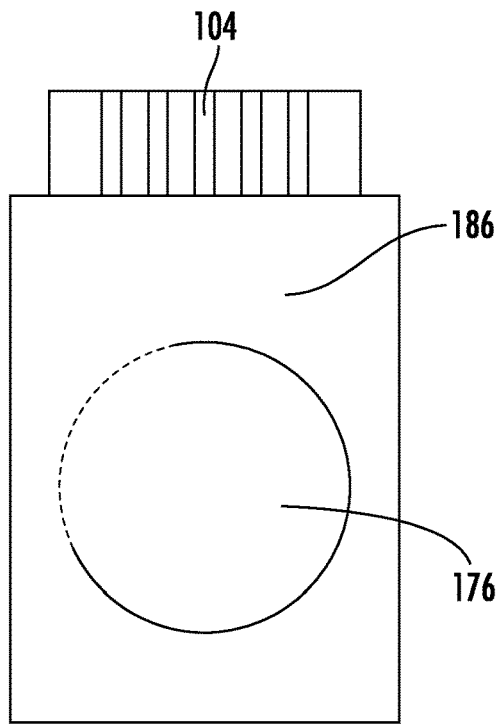
FIG. 5H is a front view of the CO sensor module in FIG. 5G with the housing removed.

Referring to FIG. 5F, the housing 161 may include a pair of tabs 106 extending from opposite sides of the housing 161. In the exemplary embodiment, the tabs 106 are located 180 degrees from each other. In alternative embodiments there may be more or less than 2 tabs 106. In alternative embodiments, the tabs 106 may be separated by more than or less than 180 degrees from each other. The tabs 106 include a groove 108 configured to receive a portion of the compartment 146 permitting the housing 161 to be inserted through the opening 162 and the tabs 106 to receive a portion of the compartment 146 locking the housing 161 into position (see FIG. 5A). The housing 161 may be removed from the compartment 146 by the user applying force to both tabs 106, in a pinching manner, disengaging the compartment 146 from the grooves 108, permitting the user to pull down the housing 161 and disengaging the housing 162 from the main board 188. The housing 161 further includes the module battery 176, the CO sensor 180 and the PCB 186 as shown in FIG. 5G and FIG. 5H.

Figure 5I:
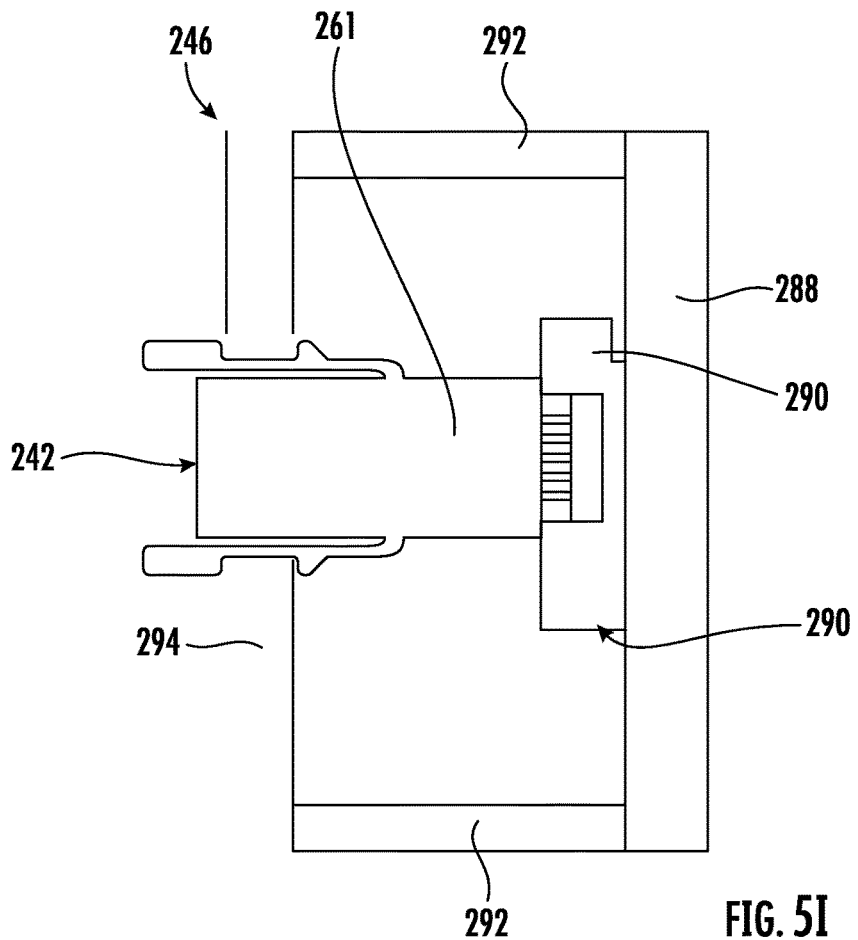
FIG. 5I is a CO sensor module installed in the control panel according to another exemplary embodiment.

Referring to FIG. 5I, an alternative embodiment of the CO sensor module 242 is shown having a connector 290 that is located between the main board 288 and the housing 261. Referring to FIG. 5I, the interior of the compartment 246 may include a pair of standoffs 292. The standoffs 292 extend from a rear wall 294 of the compartment 146 to the backside 248 of the control plate 247. The standoffs 292 provide the control plate 247 with extra stability and provide the control panel 218 with more rigidity. The standoffs 292 make it more difficult to damage the CO sensor module 242 located within the compartment 246 when force is applied to either the rear wall 294 or the control surface 244 of the control plate 247.

Figure 6A:
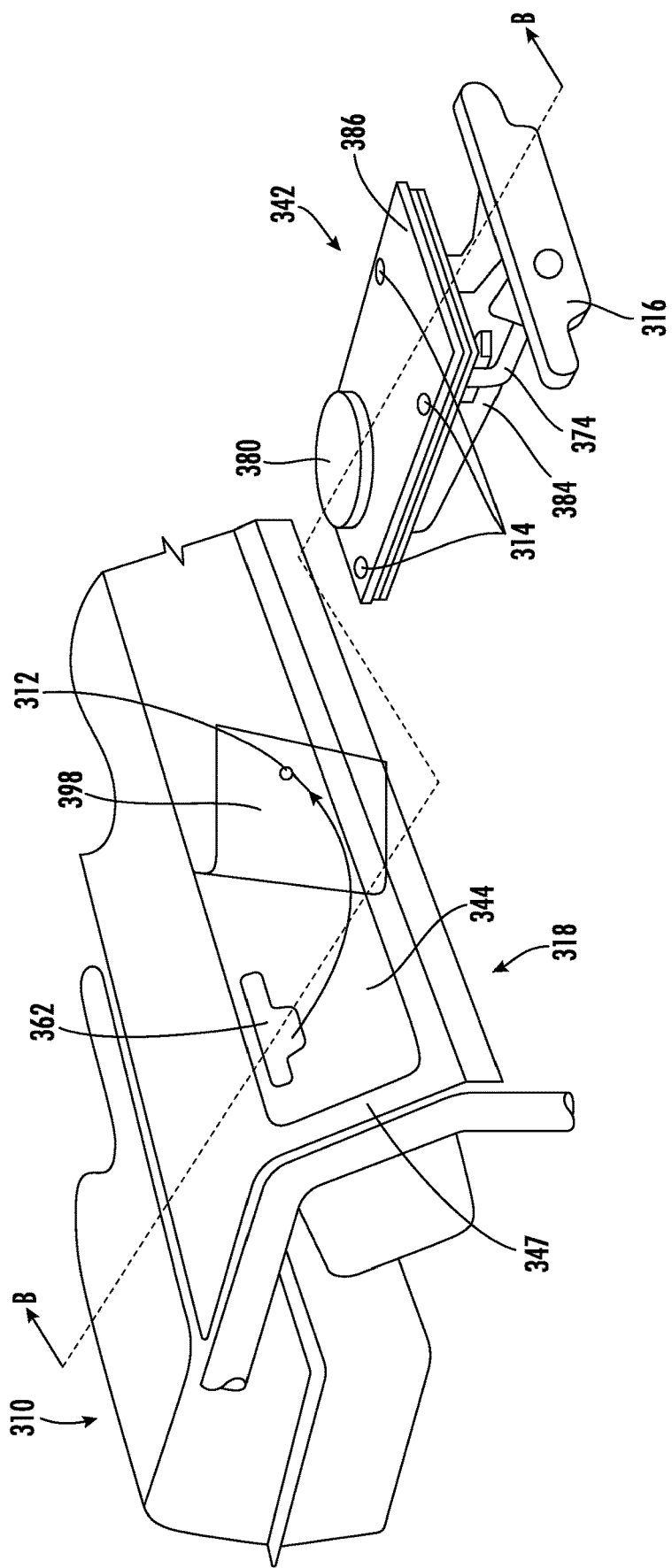
FIG. 6A is an exploded perspective view of the control panel of the portable generator and a CO sensor module according to another exemplary embodiment.

Referring to FIG. 6A, another exemplary embodiment of the CO sensor module 342 configured to be inserted into the control panel 318 of a portable generator 310 is shown. The control plate 347 includes opening 362 configured to receive a portion of the CO sensor module 342. The control surface 344 includes a decal 398. A pair of snap fit retentions 308 (see FIG. 6B) maintain the CO sensor module 342 in the stationary position when the CO sensor module 342 is properly inserted into the opening 362. The decal 398 is applied over the CO sensor module 342 using an adhesive substance or material. The decal 398 includes a light opening 312 permitting light to emit through the light pipe 374 to be seen by the user when the decal 398 is properly applied to the control surface 344. The decal 398 may be peeled back and removed when the CO sensor module 342 needs to be removed for maintenance or repairs. The decal 398 may be reused or the user may adhere a new decal 398 to the control surface 344 after the CO sensor module 342 is reinserted into the opening 362.

Figure 6B:
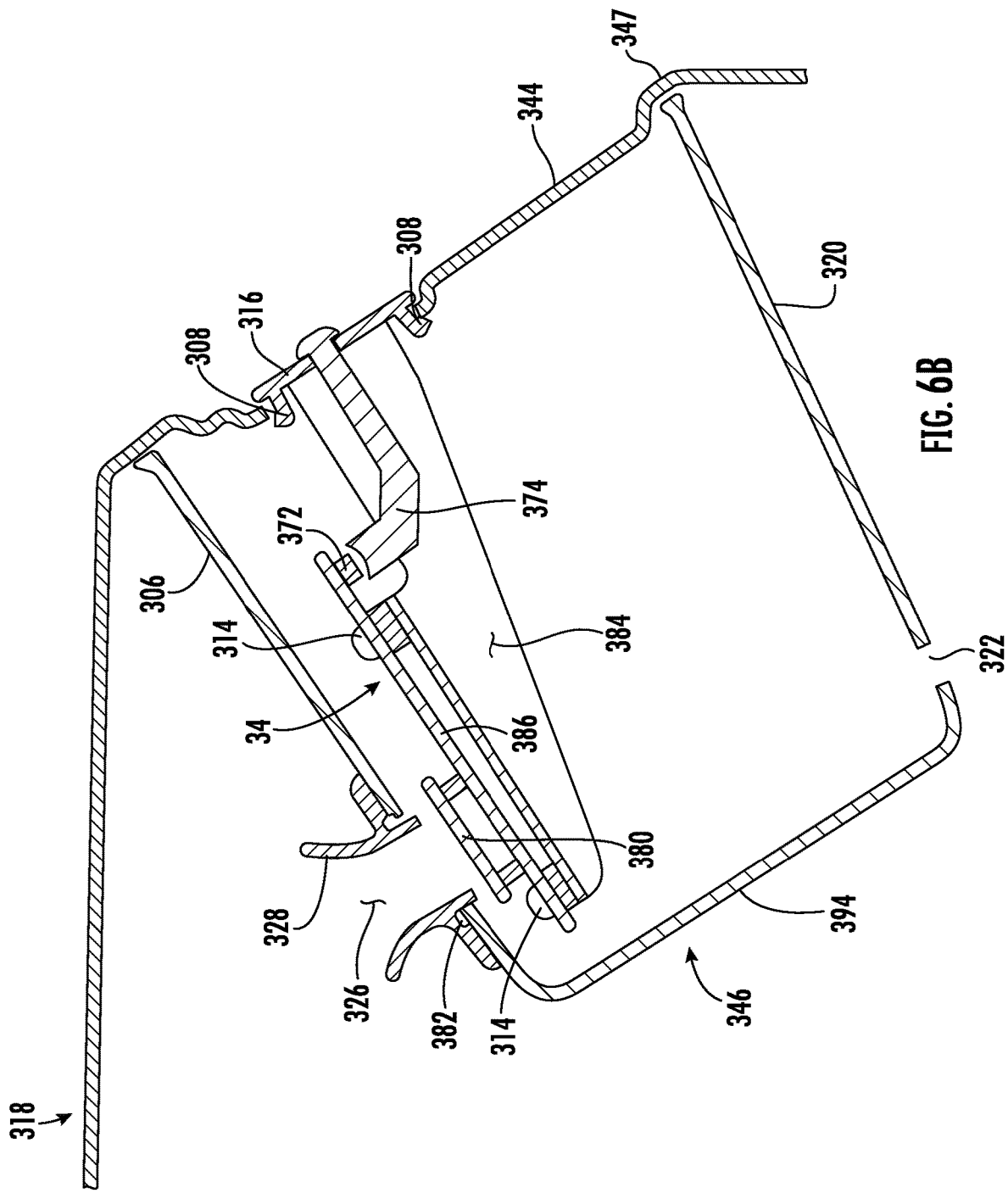
FIG. 6B is a cross-section view of the CO sensor module of FIG. 6A installed in the control panel along section line B-B in FIG. 6A.

Referring to FIG. 6A and FIG. 6B, the CO sensor module 342 is shown that includes CO sensor 380, plurality of screws 314, PCB 386, light pipe 374, LED light 372 and module frame 384. The CO sensor 380 is secured and mounted to the top surface of the PCB 386 using a bracket, screws or another type of fastening device and the PCB 386 is secured to the module frame 384 with four screws 314. The LED light 372 is affixed to the bottom surface of the PCB 386 and emits light through the light pipe 374 located below the LED light 372 to provide a visual indication of the CO sensor module 342 operating status. The light pipe 374 extends between the LED light 372 and the control surface 344 of the control plate 347 and mounted to the module frame 384. The module frame 384 of the CO sensor module 342 includes a front plate 316. The front plate 316 is flush with the control surface 344 of the control plate 347 when the CO sensor module 342 is installed properly in the control panel 318. In alternative embodiments, the PCB 386 may be secured to the module frame 384 by using more than or less than 4 screws. In alternative embodiments, the PCB 386 may be mounted using a bracket, adhesive, or various other types of fasteners to affix the PCB 386 to the module frame 384.

Referring to FIG. 6B, the compartment 346 includes a top wall 306, a bottom wall 320, a rear wall 394, a vent 322 in the bottom wall 320 extending between a pair of sidewalls 324 (not shown) and a compartment opening 326 located in the top wall 318 towards the rear wall 394. The compartment opening 326 permits the CO sensor 380 to sense the atmosphere surrounding the portable generator 310. The location of the compartment opening 326 prevents the user from easily accessing and tampering with the CO sensor 380 by disabling the CO sensor from detecting the surrounding atmosphere. An air intake horn 328 is mounted to the top wall 318 surrounding the perimeter of the compartment opening 326 to prohibit any form of moisture or debris from entering the compartment 346 and affecting the functionality of the CO sensor 380. The O-ring seal 382 is located between the top wall 318 of the compartment 346 and the air intake horn 328 to prevent moisture and debris from entering the interior of the compartment 346. The vent 322 allows for the cross-flow of atmosphere and the drainage of any form of moisture. Additionally, cross-flow for detectable atmosphere increases the detection speed of the CO sensor 380. In alternative embodiments the vent 322 may only extend a portion of the length between the pair of side walls 324.

Figure 6C:
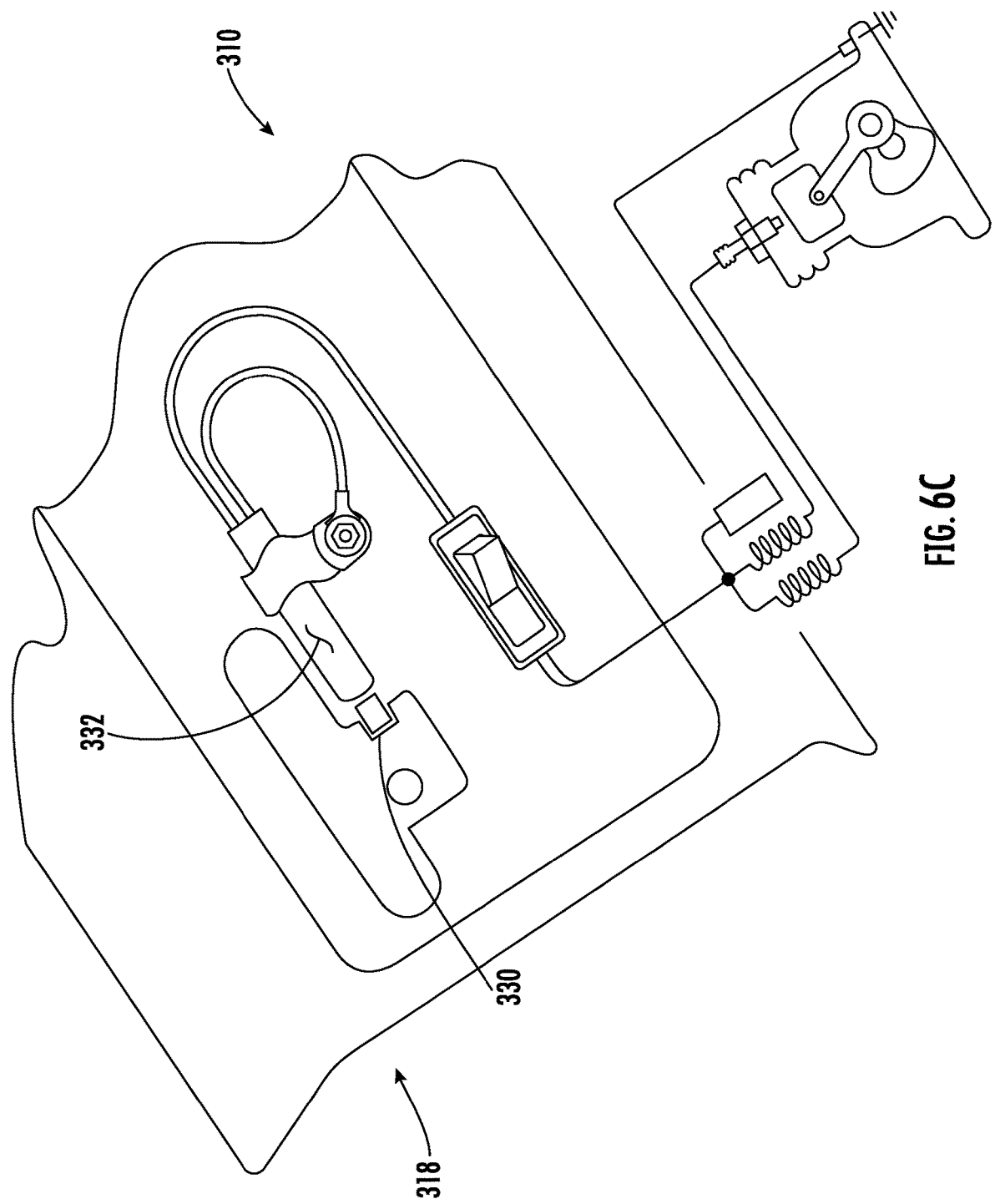
FIG. 6C is a representation of a tamper resistant CO sensor module installed in the control panel.

Referring to FIG. 6C, the CO sensor module 342 includes a magnet 330 mounted to the module frame 384. A magnetic proximity switch 332 is mounted to the control panel 318 in the open position when the magnet 330 is present. The magnetic proximity switch 332 is in the closed position when the magnet 330 is not present, e.g., the CO sensor module 342 is removed from the control panel 318. Removing the CO sensor module 342 causes the magnetic proximity switch 332 to move to the closed position grounding the ignition and preventing the operation of the generator 310. The magnetic proximity switch 332 is not visible or easily accessible by the user in order to prevent the user from tampering with the functionality of the CO sensor module 342. The control panel 318 must be disassembled to gain access to the magnetic proximity switch 332. In alternative embodiment the magnet 330 may be mounted to the module wire harness (not shown) preventing the operation of the generator 310 when the CO sensor module 342 is removed, in addition to when the module wire harness is not properly connected to the engine wire harness (not shown).

Figure 7:
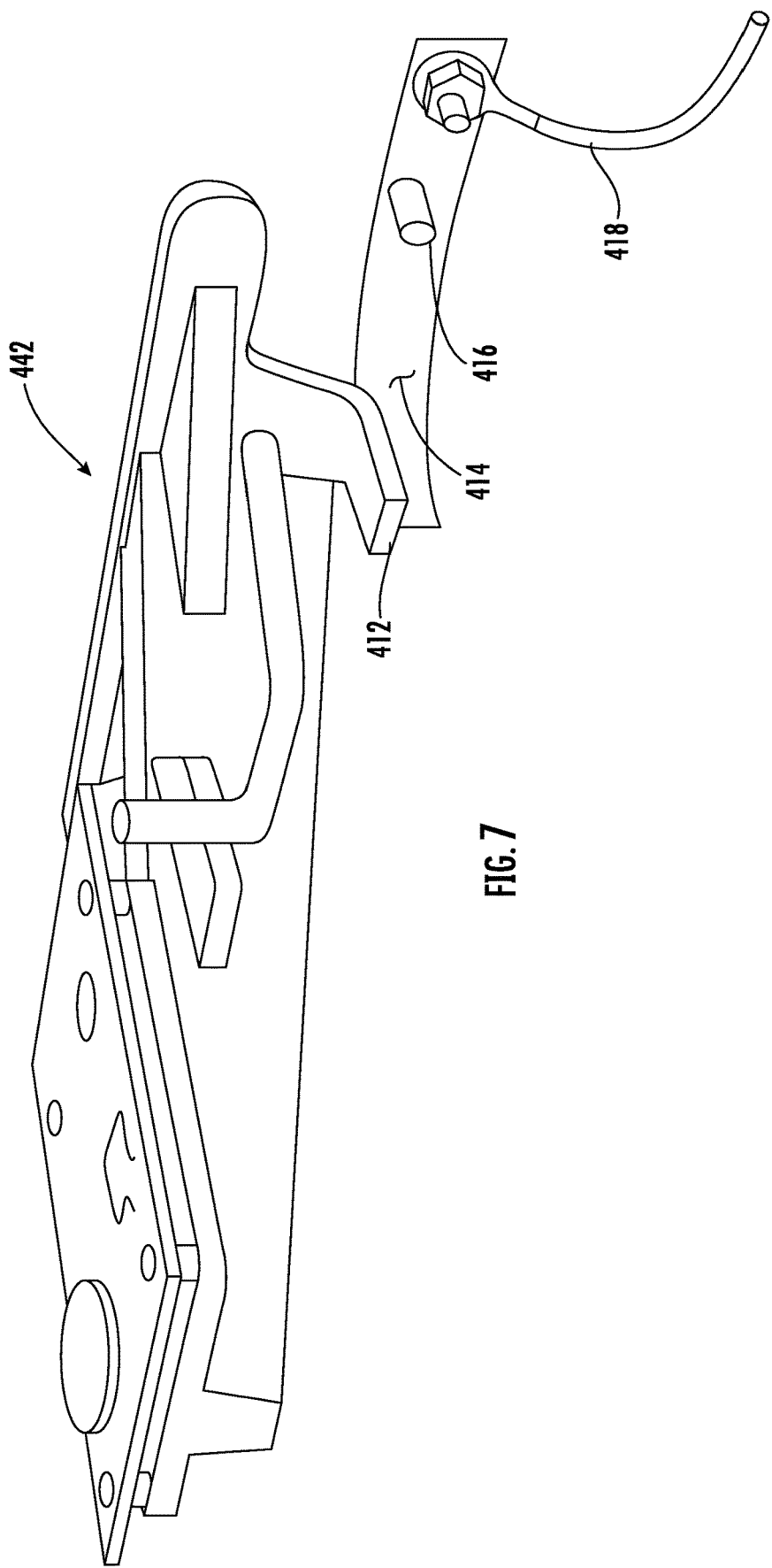
FIG. 7 is a perspective view of the CO sensor module according to another exemplary embodiment.

Referring to FIG. 7, an alternate embodiment of the CO sensor module 442 is shown. The CO sensor module includes a non-conductive tab 412, a conductive deflected beam 414, a grounded pin 416 and a wire 418 to the ignition. Removing the CO sensor module 442 causes the conductive deflected beam 414 to make contact with the grounded pin 416 putting the generator 410 in an operative state.

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

Unless described differently above, the terms "coupled," "connected," and the like, as used herein, mean the joining of two members directly or indirectly to one another. Such joining may be stationary (e.g., permanent) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the figures. It should be noted that the orientation of various elements may differ according to other exemplary embodiments, and that such variations are intended to be encompassed by the present disclosure.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

It is important to note that the construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claims.

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

An exemplary system for implementing the overall system or portions of the embodiments might include a general purpose computing computers in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

What is claimed is:

1. A generator comprising:
   an engine;
   a control panel comprising:
   a control plate having a control surface and a back side positioned opposite from the control surface; and
   a compartment coupled to the control plate, the compartment and the control plate defining an interior volume; and
   a carbon monoxide (CO) sensor module including a CO sensor, the CO sensor module positioned to extend through the control plate and into the interior volume of the compartment and removably coupled to the back side of the control plate;
   wherein the CO sensor module is configured to be removable from the control plate and replaceable with a replacement CO sensor module;
   wherein the CO sensor is configured to detect CO concentration near the generator.

2. The generator of claim 1, wherein the CO sensor module includes a housing having a first portion and a second portion, the first portion configured to be inserted into the interior volume of the compartment and the second portion configured to be positioned outside of the interior volume.

3. The generator of claim 2, wherein the first portion of the housing includes a projection extending therefrom and the second portion of the housing includes a mounting ring configured to abut the control surface of the control plate.

4. The generator of claim 3, wherein the control plate includes an opening formed in the control surface configured to receive the first portion of the CO sensor module and a recess formed in the opening configured to align with and receive the projection of the first portion upon installation of the CO sensor module into the opening.

5. The generator of claim 4, wherein the CO sensor module is rotatable between an unlocked position and a locked position.

6. The generator of claim 5, wherein in the locked position, the mounting ring abuts the control surface and the projection of the housing is not aligned with the recess.

7. The generator of claim 5, wherein in the unlocked position, the projection of the housing is aligned with the recess.

8. The generator of claim 1, wherein the CO sensor module includes a module wire harness configured to couple to an engine wire harness on the engine.

9. The generator of claim 8, wherein when the module wire harness is coupled to the engine wire harness, the engine can start, and when the module wire harness is decoupled from the engine wire harness, an ignition of the engine is grounded and the engine cannot start.

10. The generator of claim 1, wherein the CO sensor module includes a module battery providing power to the CO sensor module.

11. The generator of claim 10, wherein the CO sensor module further comprises a light-emitting diode (LED) light configured as a visual indicator to alert a user of at least one of a life of the module battery is degrading, the CO sensor is degrading, and the CO sensor module is malfunctioning.

12. The generator of claim 1, wherein the CO sensor is positioned within the housing of the CO sensor module and within the interior volume of the control panel.

* * * * *